United States Patent
Oberli et al.

(10) Patent No.: US 9,556,010 B2
(45) Date of Patent: Jan. 31, 2017

(54) DEVICE AND METHOD FOR OPENING AN AMPOULE

(71) Applicant: DEPUY SYNTHES PRODUCTS, INC., Raynham, MA (US)

(72) Inventors: Joel Oberli, Niederdorf (CH); Gunnar Rieseweber, Oberdorf (CH); Christian Roth, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 50 days.

(21) Appl. No.: 14/389,902

(22) PCT Filed: Mar. 13, 2013

(86) PCT No.: PCT/US2013/030739
§ 371 (c)(1),
(2) Date: Oct. 1, 2014

(87) PCT Pub. No.: WO2013/151696
PCT Pub. Date: Oct. 10, 2013

(65) Prior Publication Data
US 2015/0329339 A1    Nov. 19, 2015

Related U.S. Application Data

(60) Provisional application No. 61/619,756, filed on Apr. 3, 2012.

(51) Int. Cl.
*B65D 88/54* (2006.01)
*B67B 7/92* (2006.01)
(Continued)

(52) U.S. Cl.
CPC ............ *B67B 7/92* (2013.01); *A61B 17/8833* (2013.01); *A61J 1/06* (2013.01); *B01F 15/0206* (2013.01);
(Continued)

(58) Field of Classification Search
CPC ..... B05C 17/00563; B67B 7/92; B65D 47/10; B65D 47/36; B65D 1/09; B65D 1/0238; B65D 1/0253; B65D 88/54; Y10T 225/30; A61J 1/06; B65B 69/00; A61B 17/8833; A61F 2250/0071; B01F 15/0278; B01F 15/0205–15/0206; B01F 13/0023
(Continued)

(56) References Cited

U.S. PATENT DOCUMENTS 3,892,237 A * 7/1975 Steiner ............... A61M 5/2053
604/157
4,528,268 A * 7/1985 Andersen ................ C12Q 1/22
206/219
(Continued)

FOREIGN PATENT DOCUMENTS

CN      102311079 A    1/2012
JP      11-240597 A    9/1999
(Continued)

OTHER PUBLICATIONS

U.S. Appl. No. 61/619,756, filed Apr. 3, 2012, Oberli et al.

*Primary Examiner* — Paul R Durand
*Assistant Examiner* — Andrew P Bainbridge
(74) *Attorney, Agent, or Firm* — Baker & Hostetler LLP

(57) ABSTRACT

A device for opening an ampoule includes an ampoule holder configured to hold a body of the ampoule along a central longitudinal axis, a head holder configured to hold a head of the ampoule, and a guide engaged with the head holder and configured to direct the head holder from a first position on the central longitudinal axis to a second position offset from the central longitudinal axis when the ampoule holder is advanced in a first direction along the central longitudinal axis from an initial position. A method for opening an ampoule includes moving the ampoule in a first direction along a central longitudinal axis, directing the head
(Continued)

of the ampoule laterally and/or obliquely away from the central longitudinal axis to break the head of the ampoule from the body of the ampoule when the ampoule is moved in the first direction, removing material from the body of the ampoule, and removing liquid from the head of the ampoule.

35 Claims, 8 Drawing Sheets

(51) Int. Cl.
*A61B 17/88* (2006.01)
*B65D 47/36* (2006.01)
*B65D 1/09* (2006.01)
*B65D 1/02* (2006.01)
*B01F 15/02* (2006.01)
*A61J 1/06* (2006.01)

(52) U.S. Cl.
CPC .......... *B01F 15/0278* (2013.01); *B65D 1/0238* (2013.01); *B65D 1/0253* (2013.01); *B65D 1/09* (2013.01); *B65D 47/36* (2013.01); *B65D 88/54* (2013.01); *Y10T 225/30* (2015.04)

(58) Field of Classification Search
USPC ............ 222/325, 541.1–541.9, 145.5–145.6; 81/3.29; 606/92–93; 366/139, 189; 215/253, 256, 47–49; 225/97, 93, 225/103–105; 604/200; 206/219
See application file for complete search history.

(56) References Cited

U.S. PATENT DOCUMENTS

| 4,779,763 | A | * | 10/1988 | Klawitter | B65D 83/687 206/219 |
|---|---|---|---|---|---|
| 4,805,821 | A | * | 2/1989 | Kowalczyk | B26F 3/002 225/103 |
| 5,482,030 | A | * | 1/1996 | Klein | A61M 15/009 116/308 |
| 5,779,356 | A | * | 7/1998 | Chan | A61B 17/8827 366/139 |
| 6,099,510 | A | * | 8/2000 | Ruther | B67B 7/92 222/80 |
| 6,435,372 | B1 | * | 8/2002 | Blacker | A61M 15/009 128/200.23 |
| 6,516,977 | B2 | * | 2/2003 | Chan | A61B 17/8827 215/49 |
| 6,832,703 | B1 | * | 12/2004 | Scott | B67B 7/92 222/1 |
| 7,073,936 | B1 | * | 7/2006 | Jonsson | B01F 15/0226 366/139 |
| 7,175,055 | B2 | * | 2/2007 | Hansen | A61M 5/14546 222/325 |
| 7,360,674 | B2 | * | 4/2008 | Sassoon | A61L 2/18 222/1 |
| 8,256,949 | B2 | * | 9/2012 | Melsheimer | A61B 17/7097 222/246 |
| 9,272,803 | B2 | * | 3/2016 | Vogt | A61B 17/8833 |
| 2009/0171361 | A1 | * | 7/2009 | Melsheimer | A61B 17/7097 606/93 |
| 2011/0114212 | A1 | * | 5/2011 | Greter | A61B 17/8805 137/896 |
| 2012/0006874 | A1 | * | 1/2012 | Vogt | B67B 7/92 225/103 |
| 2013/0032623 | A1 | * | 2/2013 | Kayser | B67B 7/92 225/97 |

FOREIGN PATENT DOCUMENTS

| WO | WO 2010/012114 A1 | 2/2010 |
|---|---|---|
| WO | WO 2011/109915 A1 | 9/2011 |
| WO | WO 2013/151696 A1 | 10/2013 |

* cited by examiner

DEVICE AND METHOD FOR OPENING AN AMPOULE

CROSS-REFERENCE TO RELATED APPLICATIONS

This application is a National Stage Application of International Application No. PCT/US2013/030739, filed Mar. 13, 2013, which claims the benefit of U.S. Provisional Application No. 61/619,756, filed Apr. 3, 2012, the entire disclosures of both of which are incorporated herein by reference.

FIELD OF THE INVENTION

The present invention generally relates to devices for opening an ampoule. More particularly, the present invention in some embodiments relates to devices for opening an ampoule containing a material (e.g., a liquid material) and transferring the material from the ampoule to another device. Further embodiments of the invention relate to methods for opening an ampoule.

BACKGROUND OF THE INVENTION

A variety of materials, such as pharmaceuticals and other chemicals, are packaged and stored in ampoules prior to use. Ampoules typically include a cylindrical body which forms the main storage portion, a smaller tapered head portion, and a narrower neck portion therebetween. Ampoules conventionally used in the art are made from a frangible material such as glass and must be broken by the user to provide access to the material stored within. Usually the ampoule is broken at the neck portion to separate the head from the body.

Ampoules are sometimes broken by hand, which creates a number of risks for the user. For example, breaking the ampoule may release splinters and shards into the material and/or the surrounding environment. Sharp or jagged edges may also be created where the ampoule was broken which creates a hazard for the user. Moreover, the material stored in the ampoule may be volatile and/or reactive, and the user may be exposed to the material if spillage occurs during or after breaking the ampoule. The user may also be exposed to fumes released from the material once the ampoule is broken.

BRIEF SUMMARY OF THE INVENTION

The present invention according to some embodiments provides a device for opening an ampoule. In some embodiments, the device is configured to minimize or prevent exposure of the user to material (e.g., liquid material) within the ampoule or to fumes released from the material. In some embodiments, the device is configured to prevent exposure of the user to sharp or jagged edges of the opened ampoule or to splinters and shards created when the ampoule is opened. In some embodiments, the present invention provides a device that is operable using a single hand and configured to open the ampoule and transfer the material from the ampoule to a another device or container.

In some embodiments, a device for opening an ampoule containing a volume of a material (e.g., liquid material) in accordance with the present invention includes an ampoule holder configured and dimensioned to hold a body of the ampoule along a central longitudinal axis, and a head holder configured and dimensioned to hold a head of the ampoule. In some embodiments, the device includes an ampoule having a body secured to the ampoule holder and a head secured to the head holder. The device, in some embodiments, further includes a guide engaged with the head holder and configured to direct the head holder from an initial position on the central longitudinal axis to a secondary position offset from the central longitudinal axis when the ampoule holder is advanced in a first direction along the central longitudinal axis from a first position. The device is preferably configured and dimensioned for one-handed manual operation by a user and, in some embodiments, the ampoule holder is advanceable in the first direction by, for example, thumb or hand pressure applied by the user.

In some embodiments, the guide defines a path for the head holder from the initial position to the secondary position. In some embodiments, at least a portion of the path defined by the guide extends laterally and/or obliquely from the central longitudinal axis. In some embodiments, the device is configured to break the head of the ampoule from the body of the ampoule when the head holder is directed from the initial position to the secondary position by the guide. In some embodiments, the head holder is configured to apply a force sufficient to break the head of the ampoule from the body of the ampoule when the head holder is directed from the initial position to the secondary position by the guide. In some embodiments, the guide includes a rigid plane disposed at an oblique angle relative to the central longitudinal axis. In some embodiments, the head holder is configured to abut against and translate along the rigid plane when the ampoule holder is advanced in the first direction along the central longitudinal axis from the first position. In other embodiments, the guide includes a groove defining a path for the head holder from the initial position to the secondary position. In further embodiments, the guide includes a groove and the head holder includes a guide pin retained within the groove, the groove defining a path for the guide pin from the initial position to the secondary position. In some embodiments, at least a portion of the groove extends laterally and/or obliquely relative to the central longitudinal axis. In some embodiments, the head holder rotates about a pivot when the head holder is directed from the initial position to the secondary position by the guide. In some embodiments, the head holder rotates about an axis of the guide pin. In some embodiments, the head holder is rotatable about the pivot by gravitational force. In some embodiments, the head holder is configured to rotate at least 90 degrees about the pivot. In some embodiments, the head holder is configured to rotate greater than 90 degrees about the pivot. In some embodiments, rotation of the head holder about the pivot is limited to less than 180 degrees. In some embodiments, rotation of the head holder facilitates removal of material from the head of the ampoule after the ampoule is opened.

In some embodiments, the device includes a housing defining an interior space for containing the head holder and the guide. The housing includes a first end in sliding engagement with the ampoule holder according to some embodiments, and a second end proximate an outlet in fluid communication with the interior space. In some embodiments, the first end of the housing includes a handle. In some embodiments, at least a portion of the housing is transparent to allow, for example, visual inspection of the interior space. In some embodiments, the device includes a seal disposed between the ampoule holder and the housing, the seal configured to substantially prevent passage of vapor or liquid between the ampoule holder and the housing. In some embodiments, the device includes a filter disposed between the interior space and the outlet, the filter being configured (e.g., having a sufficient pore size) to allow passage of liquid from the interior space to the outlet and to prevent passage of ampoule fragments from the interior space to the outlet. In some embodiments, the housing further includes a coupling device at the outlet configured to couple with a second device.

In some embodiments, the device includes a biasing element disposed between the ampoule holder and the housing, the biasing element configured to bias the ampoule holder in a second direction opposite the first direction. In some embodiments, the biasing element is configured to apply a force to the ampoule holder in the second direction opposite the first direction. In some embodiments, the biasing element is disposed at or proximate the first end of the housing. In some embodiments, the biasing element is a coil spring disposed around the ampoule holder. The biasing element according to some embodiments is configured to return the ampoule holder substantially to the first position. In some embodiments, returning the ampoule holder substantially to the initial position (e.g., by the biasing element) creates a pressure decrease within the interior space. In some embodiments, the pressure decrease is sufficient to draw material (e.g., liquid material) from the ampoule to the interior space of the housing after the ampoule is opened. In some embodiments, the device is configured such that advancement of the ampoule holder in the first direction along the central longitudinal axis creates a pressure increase within the interior space. In some embodiments, the pressure increase within the interior space facilitates transfer of material (e.g., liquid material) from the interior space of the housing to the outlet of the housing.

In one embodiment of the present invention, a manually-operated device for breaking an ampoule includes an ampoule having a body and a head disposed about a central longitudinal axis, a housing having a wall disposed about an interior space, an ampoule holder in sliding engagement with the housing and secured to the body of the ampoule, a head holder pivotably secured to the housing and secured to the head of the ampoule within the interior space, the head holder configured to transition from an initial position on the central longitudinal axis to a secondary position offset from the central longitudinal axis to break the head of the ampoule from the body of the ampoule. In some variations of this embodiment, the device further includes a guide engaged with the head holder and configured to direct the head holder from the initial position to the secondary position when the ampoule holder is advanced along the central longitudinal axis from a first position by manual pressure. The guide, in some embodiments, includes a groove defining a path for the head holder from the initial position to the secondary position, at least a portion of the groove extending laterally and/or obliquely relative to the central longitudinal axis. In some embodiments, the head holder includes a guide pin retained within the groove and capable of translating along the groove. In some embodiments, the head holder is configured to rotate at least 90 degrees about an axis of the guide pin when the head holder is directed from the initial position to the secondary position by the guide. In other embodiments, the guide includes a rigid plane disposed at an oblique angle relative to the central longitudinal axis, the head holder configured to abut against and translate along the rigid plane when the ampoule holder is advanced in the first direction along the central longitudinal axis from the first position. The device, according to some embodiments, may also include a biasing element configured to bias the ampoule holder toward the first position when the manual pressure is released. In some embodiments, the biasing element is configured to return the ampoule holder substantially to the first position.

The present invention also provides a method for opening an ampoule containing a material (e.g., liquid). In one embodiment, a method for opening an ampoule includes moving the ampoule in a first direction along a central longitudinal axis, the body of the ampoule being disposed about the central longitudinal axis, and directing the head of the ampoule laterally and/or obliquely away from the central longitudinal axis to break the head of the ampoule from the body of the ampoule when the ampoule is moved in the first direction. In some embodiments, the ampoule is moved in the first direction by thumb pressure. In some embodiments, the method further includes removing material (e.g., liquid) from the body of the ampoule. In some embodiments, the method further includes removing material (e.g., liquid) from the head of the ampoule.

In some embodiments of the method, the head of the ampoule is disposed in the interior space of a housing and secured to a head holder pivotably engaged with the housing, and the body of the ampoule is secured to an ampoule holder configured to slide relative to the housing along the central longitudinal axis. In some embodiments, moving the ampoule in the first direction along the central longitudinal axis includes sliding the ampoule holder relative to the housing in the first direction from a first position to a second position. In some embodiments, the head holder is engaged with a guide (e.g., a rigid plane or groove) directing the head holder laterally and/or obliquely away from the central longitudinal axis when the ampoule holder is slid relative to the housing in the first direction. In some embodiments, the method further includes returning the ampoule holder substantially to the first position by sliding the ampoule holder relative to the housing in a second direction opposite the first direction. In some embodiments, the ampoule holder is returned substantially to the first position by a biasing element (e.g., a spring) disposed between the ampoule holder and the housing. In some embodiments, the method includes decreasing a pressure in the interior space of the housing as the ampoule holder is returned substantially to the first position. In some embodiments, removing liquid from the body of the ampoule includes decreasing the pressure in the interior space. In some embodiments, removing material (e.g., liquid) from the body of the ampoule is at least partially caused by decreasing the pressure in the interior space of the housing.

In some embodiments, the method further includes pivoting or rotating the head of the ampoule after breaking the head of the ampoule from the body of the ampoule. In some embodiments, removing liquid from the head of the ampoule includes pivoting the head holder after breaking the head of the ampoule from the body of the ampoule. In some embodiments, pivoting or rotating the head of the ampoule facilitates removal of material (e.g., liquid) from the head of the ampoule. In some embodiments of the method, removing material (e.g., liquid) from the head of the ampoule is caused by pivoting the head holder after breaking the head of the ampoule from the body of the ampoule. In some embodiments, the head holder is pivoted about 90 degrees. In some embodiments, the head holder is pivoted at least 90 degrees. In some embodiments, the head holder is pivoted more than 90 degrees. In some embodiments, the head holder is pivoted between 90 to 180 degrees.

In some embodiments of the method, material (e.g., liquid) is removed from the body and/or the head of the ampoule to the interior space of the housing. In some embodiments, the method further includes coupling a container to the housing and transferring the material (e.g., liquid) from the interior space of the housing to the container. In some embodiments, the method includes increasing a pressure in the interior space of the housing to facilitate transfer of the material from the interior space to the container. In further embodiments, the method includes filtering the material prior to transferring the material to the container. In some embodiments, the container includes a second material for mixing or reacting with the material from the ampoule. For example, in one embodiment, the ampoule contains a first (e.g., liquid) bone cement component and the container contains a second (e.g., dry) bone cement component.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention can be embodied in different forms and thus should not be construed as being limited to the embodiments set forth herein.

FIG. 3 shows a cross-sectional view of a device for opening an ampoule according to another embodiment of the invention; and.

DETAILED DESCRIPTION

Figure 1A:
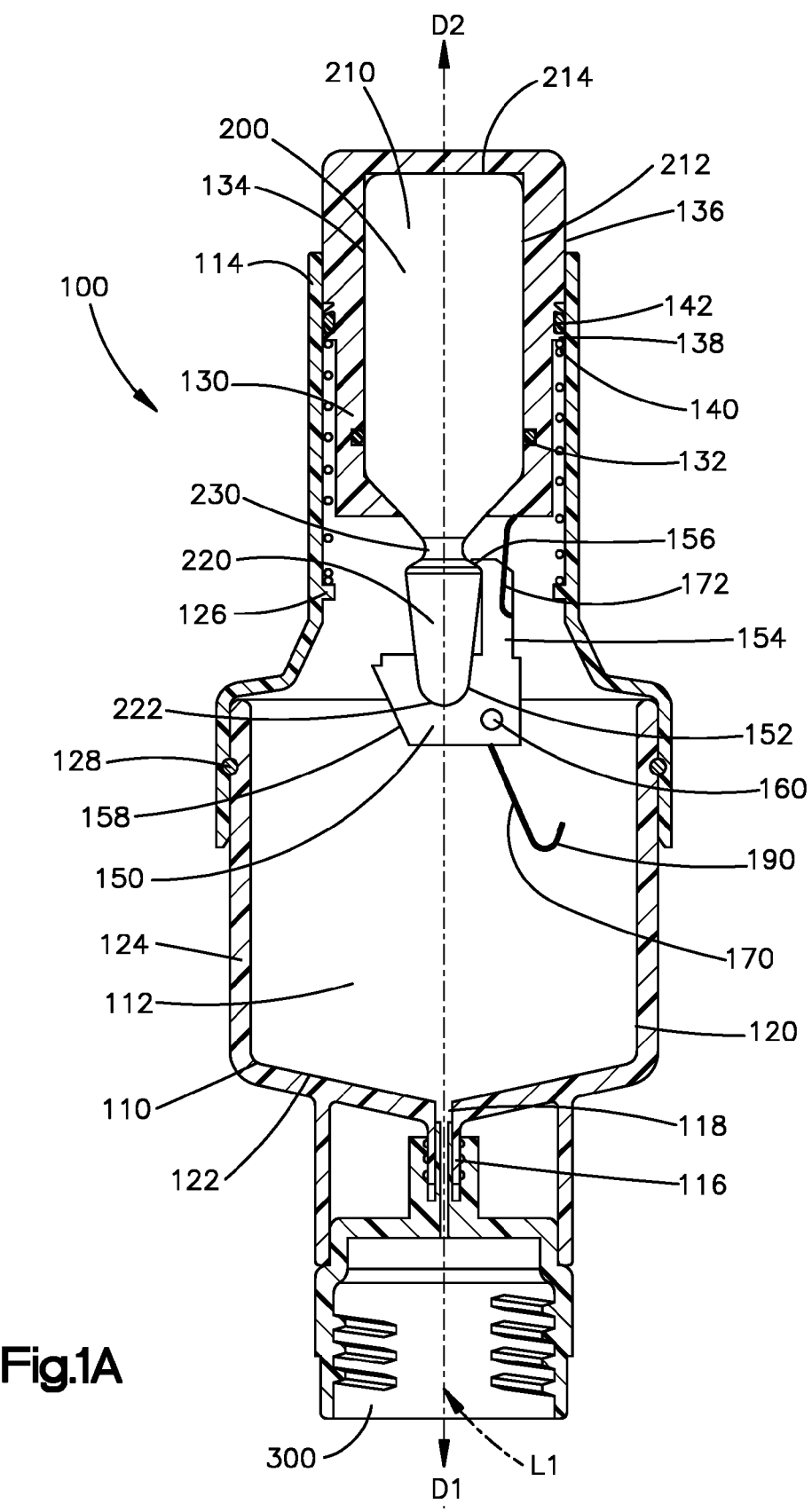
FIGS. 1A-1C show cross-sectional views of a device for opening an ampoule in sequential stages of operation according to an embodiment of the invention.
Figure 1B:
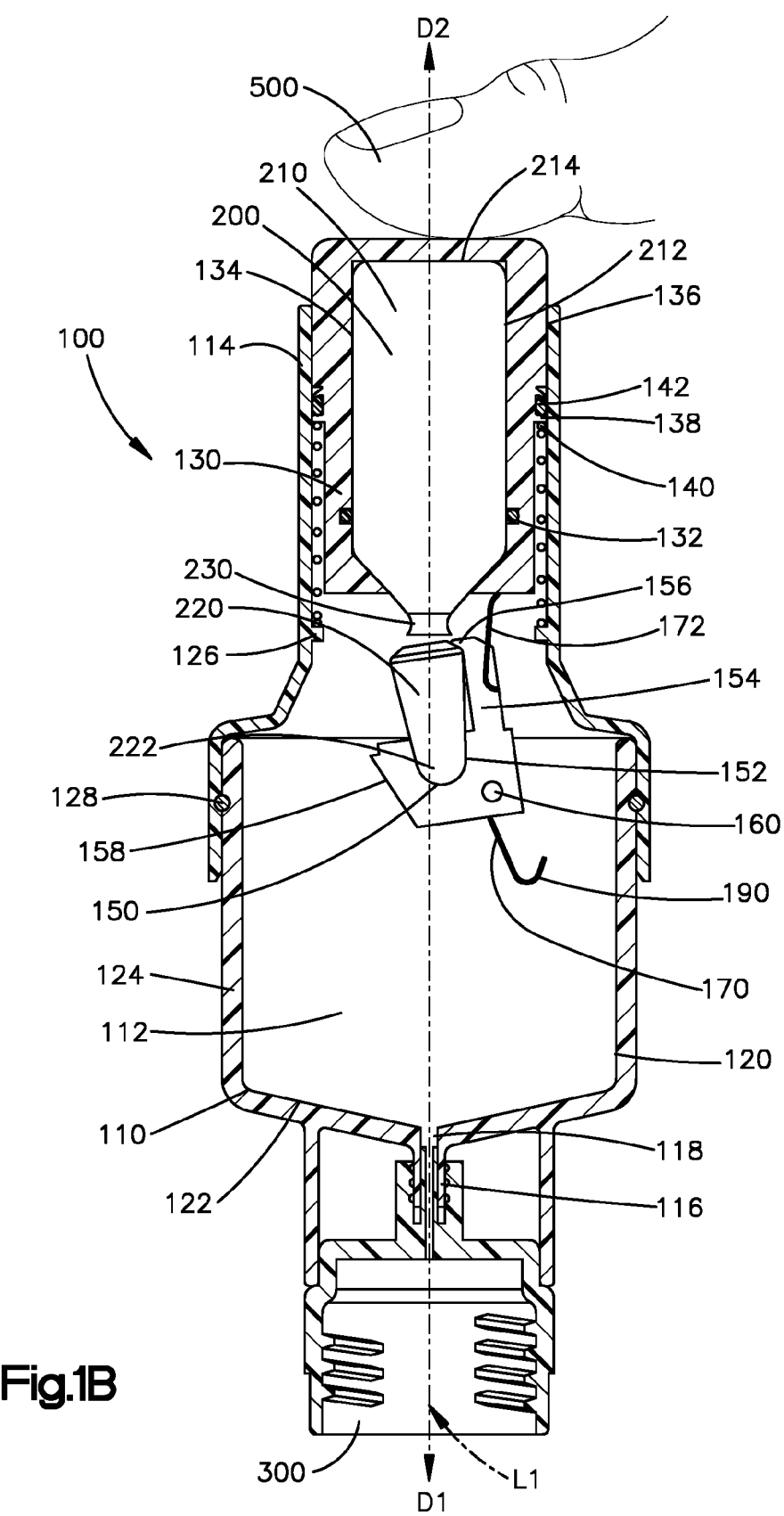

The present subject matter will now be described more fully hereinafter with reference to the accompanying Figures, in which representative embodiments are shown. The present subject matter can, however, be embodied in different forms and should not be construed as limited to the embodiments set forth herein. Rather, these embodiments are provided to describe and enable one of skill in the art. All publications, patent applications, patents, and other references mentioned herein are incorporated by reference in their entirety.

The embodiments described herein are illustrative of implementaions involving ampoules that contain liquid. This description is not intended to be limited to liquid embodiments, however. Indeed, other materials may be included in ampoules that would benefit from the present invention. Those materials may include gels, granular materials, powders, plasmas, gasseous materials, and the like. Implementations involving ampoules that contain a flowable material may benefit from the present invention for at the reasons set forth herein with respect to liquid materials.

Referring to the drawings in detail, wherein like reference numerals indicate like elements throughout, there is shown in FIGS. 1A-4C exemplary embodiments of a device 100 for opening an ampoule, for example ampoule 200, containing a material (e.g., a liquid material). In some embodiments, device 100 is further configured to transfer the material from ampoule 200 to a second device 300, for example as shown in FIGS. 1A-3. In certain preferred embodiments, device 100 is configured and dimensioned for one-handed manual operation by a user. Device 100, in a preferred embodiment, is configured to retain the fractured pieces of ampoule 200 within device 100 without causing any of the fracture pieces to impair or contaminate the material flowing from ampoule 200. In further preferred embodiments, device 100 is configured to prevent exposure of the user to sharp or jagged edges or to splinters and shards created when ampoule 200 is opened. It is also preferred that, in operation, device 100 mitigates, prevents or substantially prevents fumes, vapors, noxious gasses and like from exiting device 100 after ampoule 200 is fractured. In some embodiments, device 100 is configured to minimize, prevent, or substantially prevent exposure of the user to the material contained in ampoule 200.

The material contained in ampoule 200 may include any material conventionally packaged and stored in ampoules. In some embodiments, ampoule 200 contains a liquid material. Exemplary liquid materials that may be contained in ampoule 200 according to certain embodiments of the invention include liquid pharmaceutical products, liquid monomers, bone cement components, adhesive components, or other volatile and/or sensitive chemicals. In other embodiments, ampoule 200 may contain, for example, aromatic substances, cosmetics, foodstuffs, or health or dietary supplements.

Ampoule 200 may be configured as any conventional ampoule known in the art. In preferred embodiments, ampoule 200 is made of glass or other frangible substance capable of forming a closed container for storing material (e.g., liquid material) therein. In some embodiments, ampoule 200 includes a body 210 at a first end and a head 220 at a second end. According to some embodiments, body 210 is larger (e.g., has a larger diameter, lateral dimension, width, volume, height, and/or length) than head 220. In one embodiment, body 210 includes a generally cylindrical portion having side wall 212 and base 214. Head 220 in some embodiments may be generally tapered in shape and includes a tip 222. In further embodiments, ampoule 200 includes a neck 230 disposed between body 210 and head 220. In some embodiments, neck 230 refers to the portion of ampoule 200 having the smallest diameter between body 210 and head 220. In some embodiments, ampoule 200 includes a tapered portion where body 210 tapers to neck 230. In some embodiments, the distance between base 214 and neck 230 is greater than the distance between neck 230 and tip 222. In some embodiments, neck 230 has a diameter less than the maximum diameter of head 220, and head 220 has a maximum diameter less than the maximum diameter of body 210. According to certain embodiments of the invention, device 100 is configured to open ampoule 200 by breaking head 220 from body 210 at or proximate neck 230.

Figure 4A:
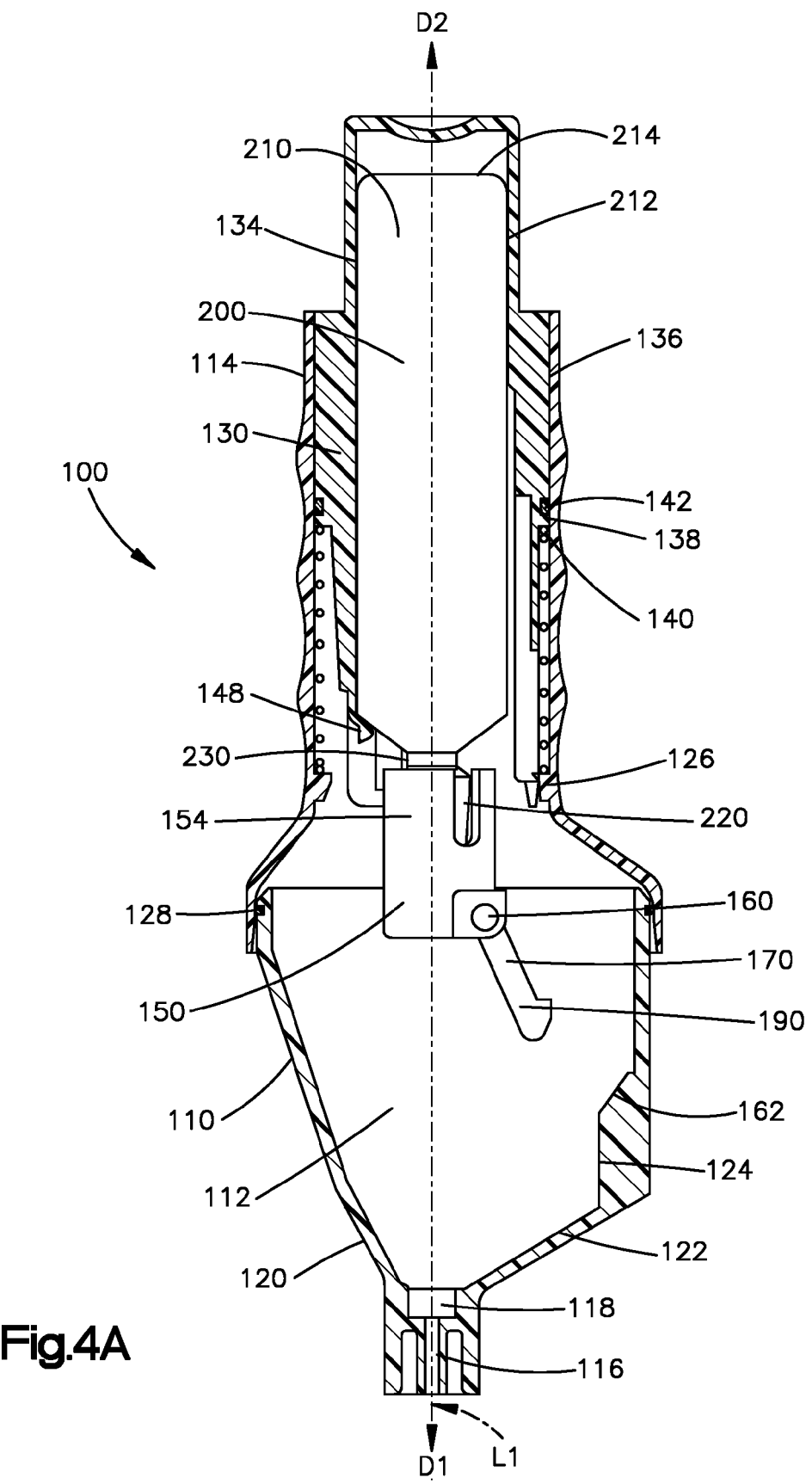
FIGS. 4A-4C show cross-sectional views of a device for opening an ampoule in sequential stages of operation according to another embodiment of the invention.
Figure 4B:
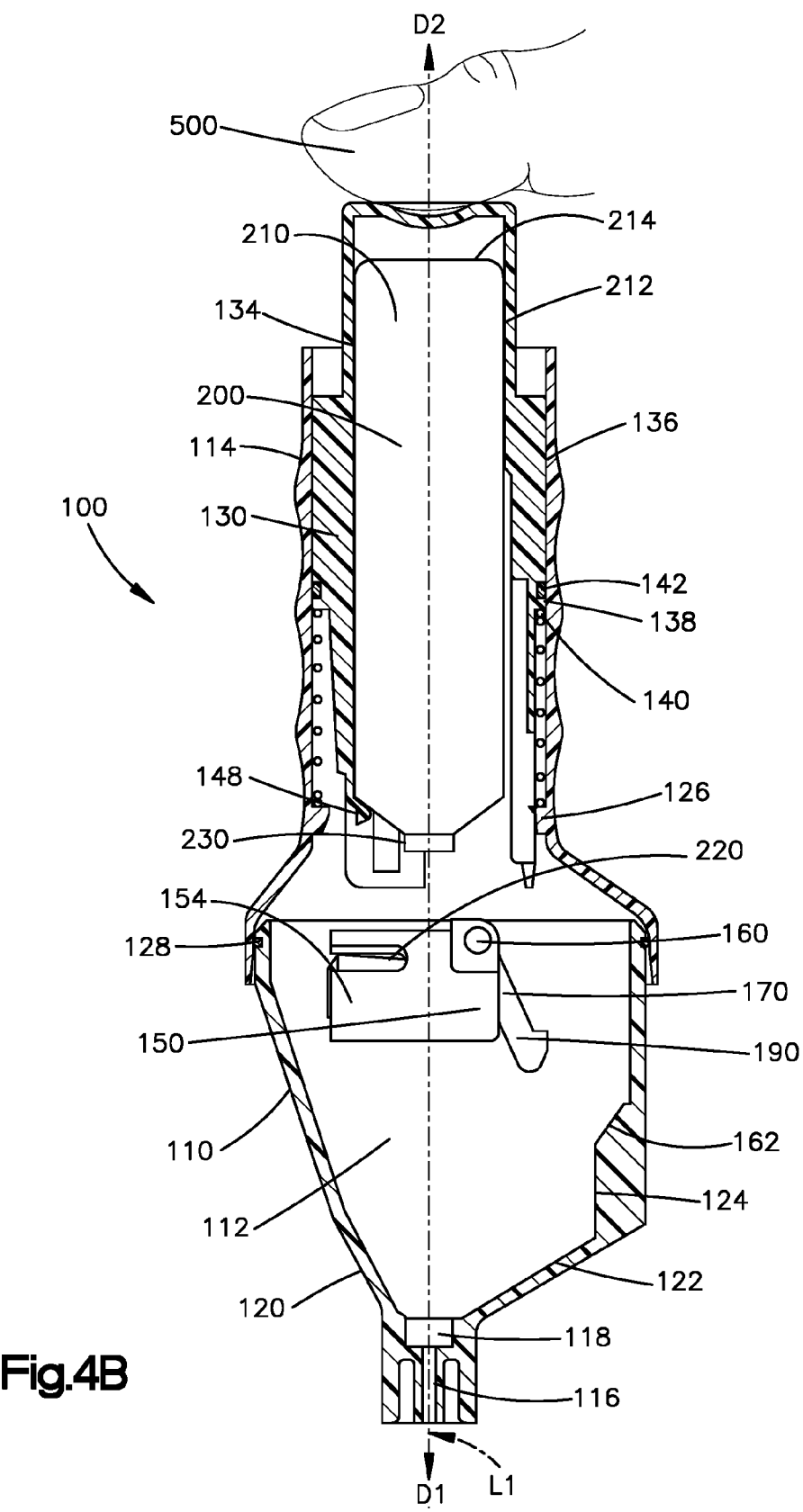
Figure 4C:
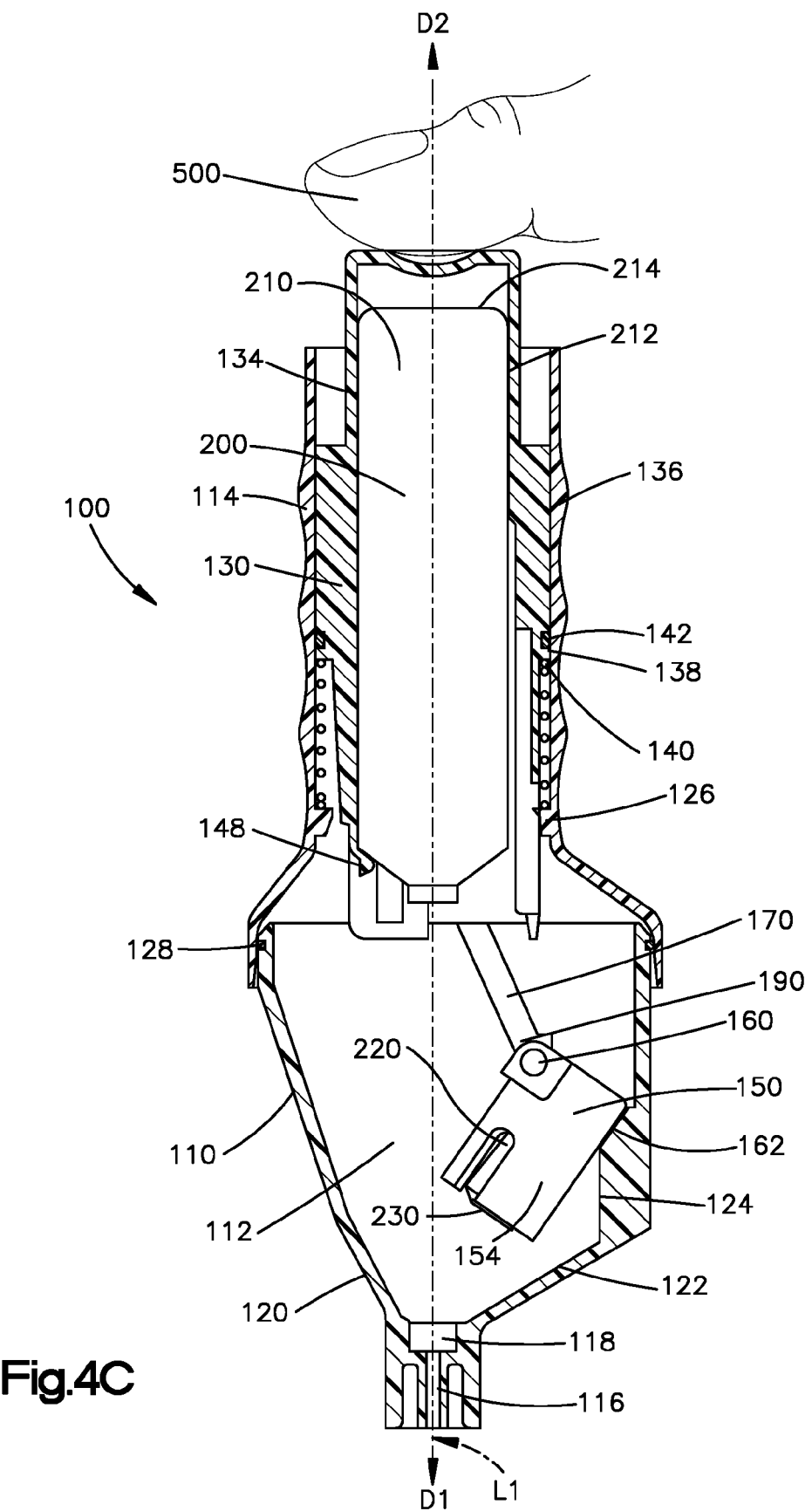

In some embodiments, device 100 is configured to firmly secure ampoule 200 within device 100 during operation. Firmly securing ampoule 200 may facilitate both a predictable breaking of ampoule 200 within device 100 and also a predictable motion of ampoule 200 within device 100 so that ampoule 200 breaks in a generally controlled way to discharge the material from ampoule 200 as described herein. In some embodiments, device 100 includes components that are configured to securely hold one or more components of ampoule 200 within device 100. According to certain embodiments of the present invention, device 100 includes an ampoule holder 130 configured and dimensioned to hold body 210 of ampoule 200. In some embodiments, body 210 is secured to ampoule holder 130. In some embodiments, body 210 is rigidly fixed to ampoule holder 130 such that body 210 cannot move or substantially move relative to ampoule holder 130 when body 210 is secured to ampoule holder 130. In some embodiments, ampoule holder 130 includes a tubular portion configured to be circumferentially disposed around body 210. In some embodiments, ampoule holder 130 is configured to completely surround at least a portion of body 210. In some embodiments, ampoule holder 130 is configured to further surround and/or enclose base 214, for example, as shown in FIGS. 4A-4C. Preferably, ampoule holder 130 is configured to position ampoule 200 such that in operation, ampoule 200 opens in a predictable and controlled fashion.

In some embodiments, ampoule holder 130 is configured to hold ampoule 200 in an exposed position relative to other functional aspects of device 100. Ampoule holder 130 may be configured so that base 214 of ampoule 200 extends beyond an open end of ampoule holder 130 when body 210 is engaged with ampoule holder 130. In some embodiments, ampoule holder 130 has a length that is less than a distance between base 214 and neck 230 of ampoule 200. In further embodiments, ampoule holder 130 is configured to not be disposed about neck 230 and/or head 220.

In some embodiments, the features of device 100 that operate to secure the position of ampoule 200 to device 100 are also configured to restrict, prevent or substantially prevent the flow of material contained within ampoule 200 when ampoule 200 is opened (e.g., broken) within device 100. In some embodiments, device 100 is configured to restrict, prevent or substantially prevent the passage of liquid or vapor between body 210 and ampoule holder 130 when body 210 is secured to ampoule holder 130. In some embodiments, ampoule holder 130 includes an interior surface 134. At least a portion of interior surface 134 of ampoule holder 130 may be configured to abut side wall 212 of body 210 when the ampoule is positioned within device 100 according to some embodiments. In some embodiments, interior surface 134 is configured to snugly secure ampoule holder 130 to ampoule 200. In some embodiments, the snug fit is created by relatively little clearance between at least a portion of interior surface 134 and at least a portion of ampoule 200 (e.g., side wall 212). In some embodiments, device 100 includes a gasket, o-ring or a deformable elastic component that engages ampoule 200 to hold it snugly within ampoule holder 130. As shown in FIGS. 1A-3, in some embodiments, interior surface 134 includes a groove having a gasket 132, such as an elastomeric O-ring, that contacts and surrounds body 210 to provide a seal between side wall 212 and ampoule holder 130. In some embodiments, as shown in FIGS. 4A-4C, ampoule holder 130 includes a lip 148 configured to engage with and secure ampoule 200 where body 210 tapers to neck 230.

In certain embodiments, the features of device 100 that operate to secure the position of ampoule 200 to device 100 are further configured to hold ampoule 200 in a particular orientation with respect to device 100 in order to facilitate opening of ampoule 200 and/or discharge of material from ampoule 200 after ampoule 200 is opened. In some embodiments, for example, device 100 is configured to hold ampoule 200 in a substantially inverted orientation so that head 220 is positioned below body 210 within device 100 during operation. In some embodiments, positioning body 210 vertically higher than head 220 facilitates discharge of material from body 210 by gravity once ampoule 200 is opened (e.g., by breaking head 220 from body 210). In some embodiments, ampoule holder 130 is configured to hold body 210 of ampoule 200 in a particular orientation with respect to device 100. In some embodiments, ampoule holder 130 is configured and dimensioned to hold body 210 of ampoule 200 along a central longitudinal axis L1 of device 100. In some embodiments, when body 210 is secured to ampoule holder 130, body 210 is oriented so that side wall 212 is radially disposed about central longitudinal axis L1. Device 100, in preferred embodiments, may be oriented during operation so that central longitudinal axis L1 is substantially aligned with a vertical axis.

Figure 1C:
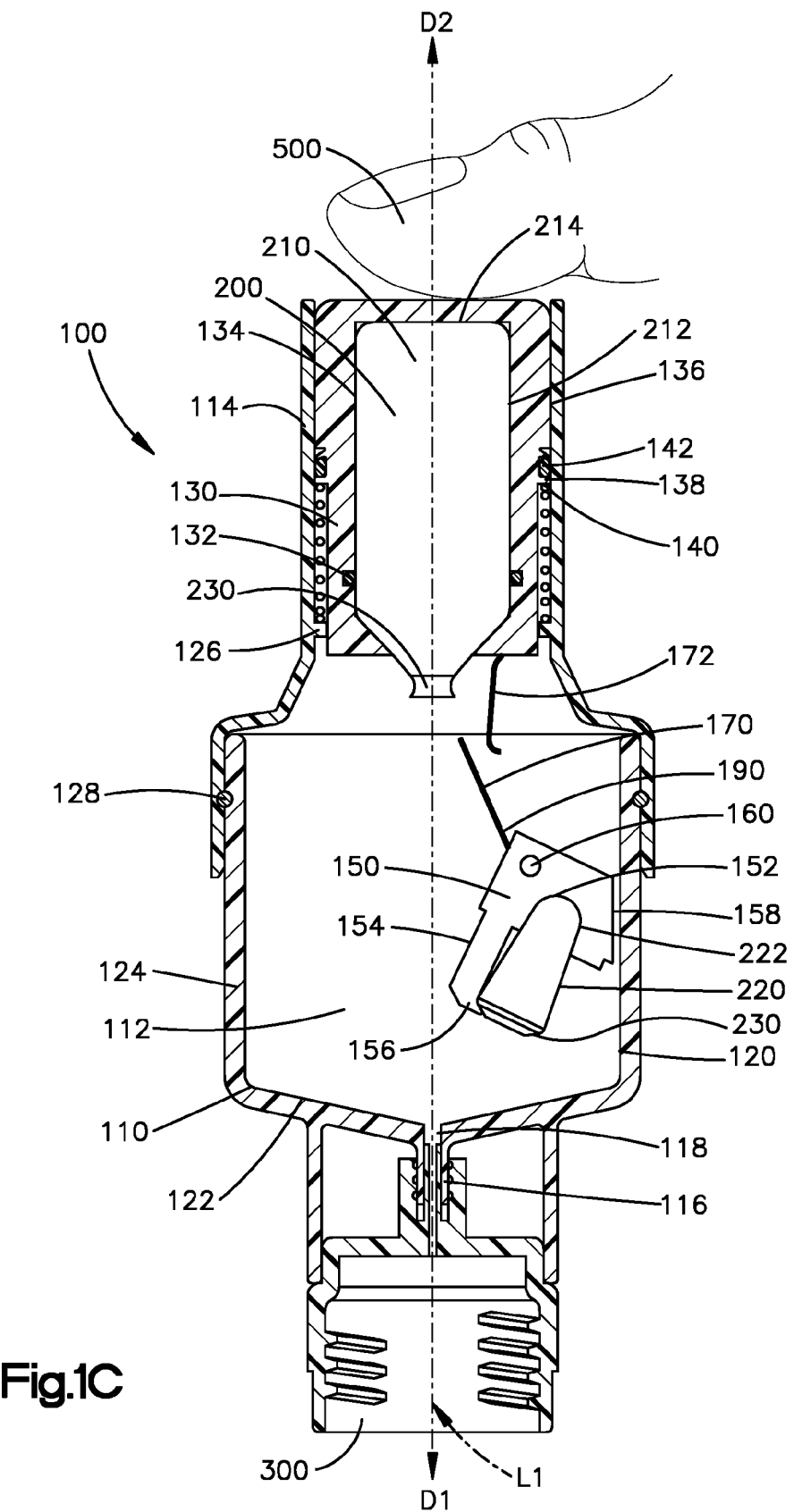

In some embodiments, device 100 is actuated by moving ampoule holder 130, with body 210 secured thereto, relative to one or more other components of device 100. In some embodiments of device 100, ampoule holder 130 mates with (e.g., is received within) a housing 110. Housing 110 in preferred embodiments is configured to provide an enclosure for receiving ampoule 200 and the material discharged from ampoule 200 after ampoule 200 is opened. In some embodiments, housing 110 is configured to receive and at least partially enclose body 210 of ampoule 200. In some embodiments, housing 110 is configured to receive and enclose at least head 220 of ampoule 200. In some embodiments, housing 110 is configured to receive and enclose at least head 220 and neck 230 of ampoule 200. In some embodiments of device 100, housing 110 is configured to receive ampoule 200 by receiving ampoule holder 130 secured to ampoule 200. In further embodiments, housing 110 is configured to receive ampoule holder 130 in a sliding engagement therewith. In some embodiments, ampoule holder 130 is configured to move with respect to housing 110 when received therein to allow relative movement between housing 110 and ampoule 200. In some embodiments, during operation of device 100, ampoule holder 130 is displaced toward housing 110 from a first position to a second position relative to housing 110. In some embodiments, ampoule holder 130 is movable with respect to housing 110 between a first position, where at least a portion of ampoule holder 130 extends outside of housing 110 (e.g., as shown in FIGS. 1A and 4A), and a second position, where ampoule holder 130 is situated further or entirely inside housing 110 relative to the first position (e.g., as shown in FIGS. 1C and 4C). In some embodiments, actuation of device 100 includes moving ampoule holder 130 from the first position to the second position, for example, advancing ampoule holder 130 into housing 110.

Device 100 is preferably configured to limit or restrict the movement of ampoule holder 130 with respect to housing 110. Limiting the movement of ampoule holder 130 may facilitate a predictable motion of ampoule 200 within device 100 so that ampoule 200 breaks in a generally controlled way to discharge the material from ampoule 200 as described herein. In some embodiments, device 100 is configured so that ampoule holder 130 is movable with respect to housing 110 between a first position and a second position along central longitudinal axis L1. In some embodiments, device 100 is configured so that ampoule holder 130 is configured to move with respect to housing 110 only in first and second directions along central longitudinal axis L1 (e.g., as indicated by arrows D1 and D2, respectively). In some embodiments, device 100 is configured so that ampoule holder 130 is not rotatable with respect to housing 110 (e.g., about central longitudinal axis L1) when ampoule holder 130 is received therein.

In some embodiments of device 100, ampoule holder 130 is received at a first end of housing 110, which may be configured to limit the motion of ampoule holder 130 with respect to housing 110 as described herein. In some embodiments, the first end of housing 110 is configured as an inlet portion 114 for receiving ampoule holder 130 and ampoule 200 therein. In some embodiments, ampoule holder 130 is received in inlet portion 114 in sliding engagement therewith. In some embodiments, inlet portion 114 is radially disposed about and configured to receive ampoule holder 130 along central longitudinal axis L1. Inlet portion 114, according to some embodiments, includes a tubular section configured to be circumferentially disposed around at least a portion of ampoule holder 130. In some embodiments, at least a portion of ampoule holder 130 and/or ampoule 200 secured thereto may extend out of inlet portion 114. Preferably, device 100 is further configured to minimize, prevent or substantially prevent the passage of liquid or vapor between inlet portion 114 and ampoule holder 130 when ampoule holder 130 is received in inlet portion 114. For example, device 100 may be configured to include a seal between inlet portion 114 and ampoule holder 130 to prevent the escape of liquid or vapor. In some embodiments, exterior surface 136 of ampoule holder 130 includes a groove having a gasket 142, such as an elastomeric O-ring, that provides a seal between exterior surface 136 and inlet portion 114 configured to prevent the passage of liquid or vapor.

Device 100, according to certain embodiments, is configured to be manually operated by a user. In some embodiments, during operation of device 100, ampoule holder 130 may be manually displaced by the user from a first position to a second position relative to housing 110. In some embodiments, ampoule holder 130 is configured to be depressed into housing 110 from a first position to a second position by the application of manual pressure from a user, for example, by thumb 500 of the user (e.g., as shown FIGS. 1B, 1C, 4B, and 4C) or by the palm and/or fingers of the user. In one embodiment, the user may press against the portion of ampoule holder 130 and/or ampoule 200 secured thereto that extends out of inlet portion 114 in some embodiments. In further embodiments as described herein, it may also be desirable to return ampoule holder 130 substantially to the first position after the manual pressure is released. In certain embodiments, device 100 may further include a biasing element 140 (e.g., a spring) configured to bias ampoule holder 130 from the second position towards the first position in order to facilitate return of ampoule holder 130 substantially to the first position once the pressure is released from ampoule holder 130. In some embodiments, biasing element 140 is configured to substantially maintain ampoule holder 130 at the first position until sufficient pressure is applied to press ampoule holder 130 towards the second position. In some embodiments of device 100, biasing element 140 is disposed between housing 110 and ampoule holder 130. In some embodiments, biasing element 140 is disposed between ampoule holder 130 and inlet portion 114. In some embodiments, biasing element 140 includes one or more coil springs disposed around at least a portion of ampoule holder 130. In some embodiments, biasing element 140 extends between an inner flange 126 of inlet portion 114 and an outer flange 138 on exterior surface 136 of ampoule holder 130. In some embodiments, biasing element 140 is configured to become compressed when ampoule holder 130 is advanced in first direction D1 along central longitudinal axis L1. In some embodiments, biasing element 140 is configured to bias ampoule holder 130 in second direction D2 along central longitudinal axis L1. In some embodiments, biasing element 140 is configured to return ampoule holder 130 substantially to the first position when the manual pressure of the user is released.

Figure 2:
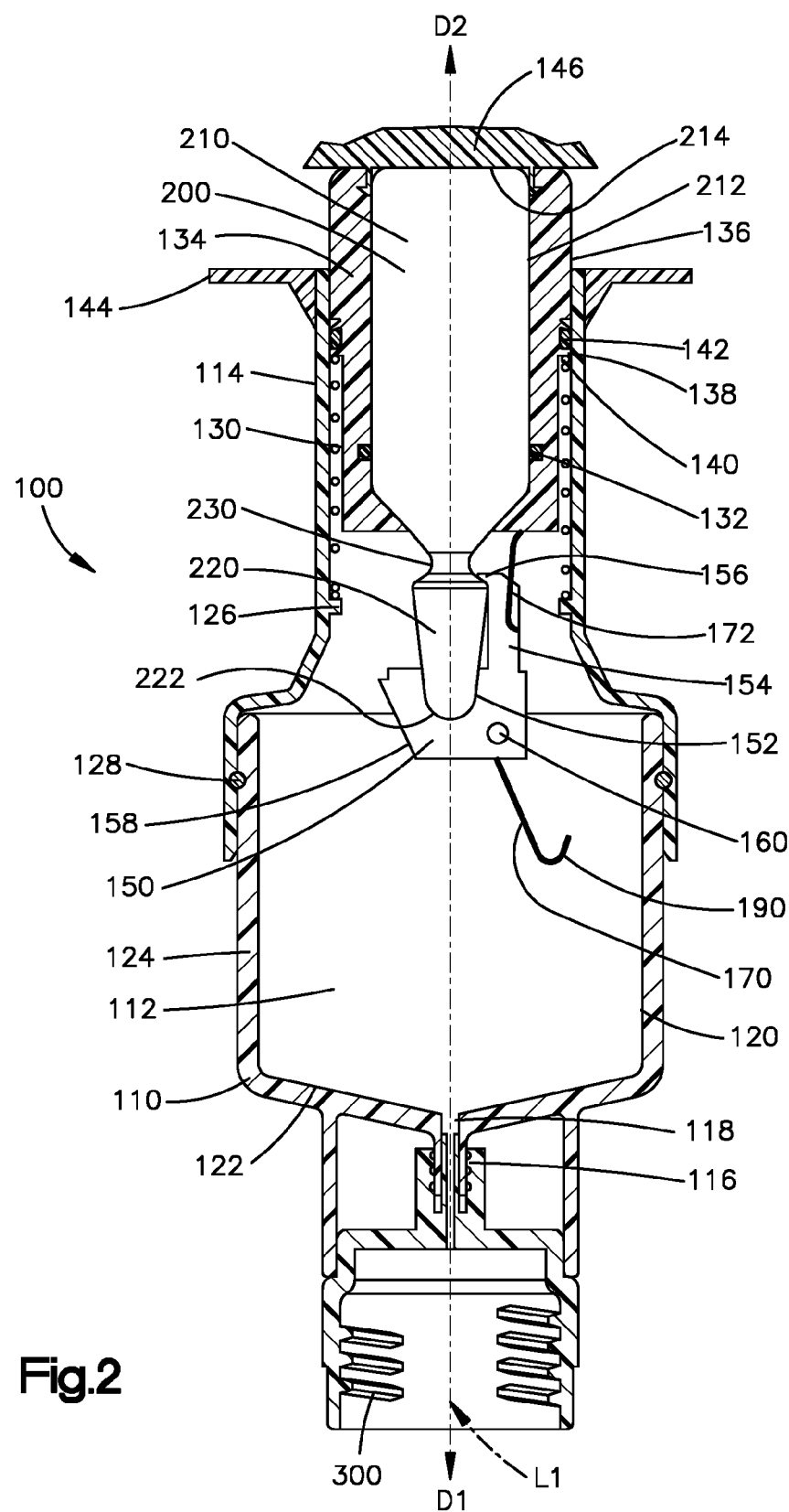
FIG. 2 shows a cross-sectional view of a device for opening an ampoule according to an embodiment of the invention.

Device 100 is preferably configured and dimensioned to be a handheld device and includes features configured to facilitate manual operation by the user according to some embodiments. In further preferred embodiments, device 100 is configured to be operable using only a single hand. In some embodiments, for example, inlet portion 114 of housing 110 is configured and dimensioned as a handle that may be gripped by the fingers and palm of a user's hand. As such, inlet portion 114 may be textured or include finger grooves to facilitate gripping by the user according to some embodiments. Thumb 500 of the user may remain free to actuate device 100, for example, by pressing ampoule holder 130 into housing 110 as depicted in FIGS. 1B, 1C, 4B and 4C. Referring to FIG. 2, device 100 may include one or more finger grips 144 on the exterior of inlet portion 114 in some embodiments. In some embodiments, where ampoule holder 130 does not enclose base 214, device 100 may further include an end cap 146 securable to the end of ampoule holder 130 to enclose base 214 of ampoule 200, for example, to prevent direct contact between the user and ampoule 200 and to protect the user from accidental breakage of ampoule 200. In some embodiments, end cap 146 is securable to ampoule holder 130 by a snap fit or interference fit. In some embodiments, finger grips 144 and/or end cap 146 may provide for improved ergonomics and allow the user to apply greater force onto ampoule holder 130, for example, to facilitate depressing ampoule holder 130 into housing 110 from the first position to the second position during operation of device 100.

As described herein, actuation and operation of device 100 includes advancing ampoule holder 130, secured to ampoule 200, from a first position to a second position. In some embodiments, operation of device 100 includes advancing ampoule holder 130 from a first position to a second position along central longitudinal axis L1. In some embodiments, operation of device 100 includes advancing ampoule holder 130 into housing 110, as shown for example in FIGS. 1B, 1C, 4B, and 4C. During operation of device 100 in some embodiments, device 100 is configured to open ampoule 200 by applying a force to ampoule 200 sufficient to break head 220 from body 210 when ampoule holder 130, secured to ampoule 200, is advanced from the first position to the second position. In some embodiments, device 100 is configured to apply a force to head 220 and/or neck 230 during operation sufficient to break head 220 from body 210. In some embodiments, device 100 is configured to apply a force to head 220 and/or neck 230 directed laterally and/or obliquely relative to central longitudinal axis L1.

In some embodiments, device 100 includes a component configured to apply a force to head 220 and/or neck 230 sufficient to break head 220 from body 210. In some embodiments, the component that is configured to applying a force to head 220 and/or neck 230 is further configured to securely retain head 220 before, during, and after breaking head 220 from body 210. Retaining head 220 after breaking head 220 from body 210 may be advantageous in some embodiments because it may allow for further manipulation of head 220, for example, to facilitate removal of material that remains contained in head 220 after breaking ampoule 200. In further embodiments, device 100 is configured to pivot or rotate the separated head 220, for example, to facilitate discharge material that may be contained in head 220. Referring again to FIGS. 1A-4C, device 100 according to certain embodiments of the present invention includes a head holder 150 configured and dimensioned to hold head 220 of ampoule 200. In some embodiments, head holder 150 is positioned within housing 110. In some embodiments, head holder 150 is movable within housing 110. In some embodiments, head holder 150 is pivotably engaged with housing 110. In certain preferred embodiments, head 220 is secured to head holder 150 in an initial position before ampoule 200 is broken. In some embodiments, both head 220 and head holder 150 are positioned on central longitudinal axis L1 in the initial position (FIGS. 1A and 4A). In some embodiments, head holder 150 is configured to be rigidly fixed to head 220 so that head 220 cannot move relative to head holder 150 when head 220 is secured to head holder 150. In some embodiments, head holder 150 is configured to at least partially surround head 220. Referring to FIGS. 1A-2, in some embodiments, head holder 150 includes a recess 152 configured to receive at least a portion of head 220. In some embodiments, recess 152 is configured to receive tip 222. In some embodiments, head holder 150 further includes a portion 154 that extends along a side of head 220 and includes a lip 156 that engages with ampoule 200 at or proximate neck 230. In some embodiments, portion 154 circumferentially extends around at least a portion of head 220, for example, as shown in FIGS. 4A-4C. In some embodiments, head holder 150 is made entirely from a rigid material, such as a rigid plastic. Head holder 150, according to other embodiments, may be constructed from more than one material. In some embodiments, for example, a portion of head holder 150 which contacts head 220 may be made from a flexible and/or elastomeric material configured to form a tight or snug fit around head 220 while the remainder of head holder 150 may be formed from a rigid material, such as a rigid plastic.

Device 100 is preferably configured so that head holder 150, while secured to head 220, applies a force to ampoule 200 sufficient to break head 220 from body 210 during operation of device 100 in order to open ampoule 200. Preferably, device 100 is configured so that head 220 is broken from body 210 while enclosed by housing 110 to prevent escape of material and/or fractured pieces of ampoule 200. In some embodiments, device 100 is configured to direct head holder 150 laterally and/or obliquely relative to ampoule 200 while head holder is secured to head 220 to cause head holder 150 to break head 220 from body 210. In further embodiments, device 100 is configured to direct head holder 150 laterally and/or obliquely when ampoule holder 130 is advanced from the first position to the second position as described herein. In some embodiments, device 100 includes a guide 190 configured to direct head holder 150 from an initial position (e.g., before ampoule 200 is opened) to a secondary position. In some embodiments, guide 190 defines a path for head holder 150 from the initial position to the secondary position, at least a portion of the path extending laterally and/or obliquely relative to central longitudinal axis L1. In some embodiments, where central longitudinal axis L1 is substantially aligned with a vertical axis, the secondary position is lower than the initial position. In some embodiments of device 100, head holder 150 is engaged with a guide 190 configured to direct head holder 150 from an initial position on the central longitudinal axis L1 to a secondary position laterally and/or obliquely offset from central longitudinal axis L1 when ampoule holder 130 is advanced relative to housing 110 from a first position to a second position as described herein, for example, when ampoule holder 130 is advanced along central longitudinal axis L1 relative to housing 110. In some embodiments, when head holder 150 is directed laterally and/or obliquely from the initial position to the secondary position by guide 190, the lateral and/or oblique movement of head holder 150 applies a force sufficient to break head 220 secured thereto from body 210, thereby opening ampoule 200.

As illustrated in FIGS. 1A-1C and 4A-4C, guide 190 according to one embodiment of the present invention includes a groove 170. In some embodiments, at least a portion of groove 170 is configured to extend laterally relative to central longitudinal axis L1. In some embodiments, at least a portion of groove 170 is configured to extend in a direction substantially oblique to central longitudinal axis L1. In some embodiments, groove 170 is disposed within housing 110. In some embodiments, groove 170 is formed in an inner wall of housing 110. In some embodiments, head holder 150 is engaged with groove 170 and is configured to translate along groove 170 from an initial position to a secondary position. According to some embodiments, head holder 150 includes a guide pin 160 retained within and movable along groove 170. In some embodiments, head holder 150 is configured to translate along groove 170 from the initial position to the secondary position during operation of device 100 when ampoule holder 130 is advanced from the first position to the second position as described herein. For example, with reference to FIGS. 1B, 1C, 4B and 4C, in some embodiments, as ampoule holder 130 is advanced along central longitudinal axis L1 in first direction D1 (e.g., by being pressed by thumb 500), groove 170 directs guide pin 160 and head holder 150 obliquely away from central longitudinal axis L1, thereby causing head 220 to break from body 210 proximate neck 230 and allowing withdrawal of the material stored in ampoule 200 as described herein.

Figure 3:
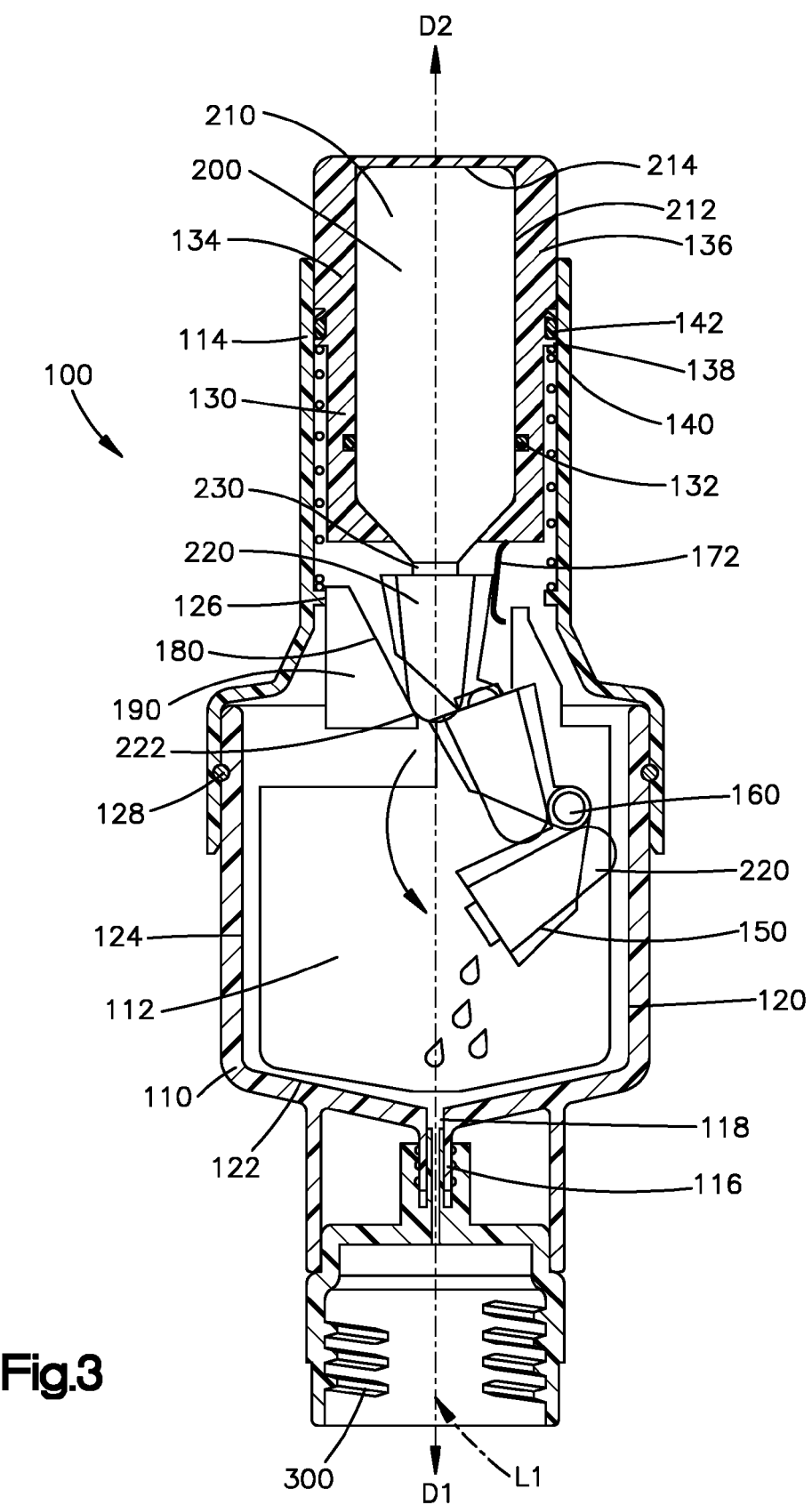

FIG. 3 shows a guide 190 according to another embodiment of the present invention. According to this embodiment, guide 190 alternatively or further includes a rigid plane 180 that is obliquely angled relative to central longitudinal axis L1. In some embodiments, rigid plane 180 is disposed within housing 110. In some embodiments, rigid plane 180 is secured to or formed from an inner wall of housing 110. In some embodiments, rigid plane 180 is engaged with head holder 150. In some embodiments, rigid plane 180 is configured to abut head 220 and/or head holder 150. In some embodiments, head holder 150 is configured to translate along rigid plane 180 from an initial position to a secondary position during operation of device 100 when ampoule holder 130 is advanced from the first position to the second position as described herein. For example, in some embodiments as ampoule holder 130 is advanced along central longitudinal axis L1 in first direction D1, head 220 and/or head holder 150 is forced against and directed obliquely by rigid plane 180, thereby causing head 220 to break from body 210 and allowing withdrawal of the material stored in ampoule 200 as described herein.

Device 100, in some embodiments, is further configured to manipulate head 220 after head 220 is broken from body 210. In some embodiments, device 100 is configured to remove material (e.g., liquid material) contained in head 220 after breaking ampoule 200 to ensure that all or substantially all the material contained in ampoule 200 is collected. Collecting all or substantially all the material contained in ampoule 200 may be particularly important where the material is to be used in applications requiring substantially exact amounts (e.g., in dosing a pharmaceutical product or in the preparation of bone cements). In some embodiments, device 100 is configured to rotate or pivot head 220 after separation of head 220 from body 210, for example, to facilitate removal of material contained in head 220. In some embodiments, device 100 is configured to rotate or pivot head 220 so that the open end of head 220 formed after separation from body 210 is pointed downwardly and material may be withdrawn from head 220 by gravity. In some embodiments, rotation or pivoting of head 220 may also facilitate removal of material from head 220 by centrifugal force. Referring now to FIGS. 1C, 4B and 4C, after head 220 is separated from body 210, head 220 remains secured to head holder 150 according to certain preferred embodiments of the invention. In some embodiments, head holder 150 is rotatable about guide pin 160 as head holder 150 is directed to the secondary position along groove 170 after head 220 is broken from body 210. In some embodiments, head holder 150 is rotatable about guide pin 160 by gravitational force. In some embodiments, head holder 150 is rotatable about an axis of guide pin 160, for example, which may be non-intersecting with and/or oriented substantially orthogonal to central longitudinal axis L1. In some embodiments, as shown in FIGS. 1A-3, device 100 may include a spring 172 configured to apply a force to head holder 150 to cause rotation of head holder 150 about guide pin 160 after head 220 is broken from body 210. In some embodiments, spring 172 is configured to apply a force to portion 154 of head holder 150. In some embodiments, spring 172 may be disposed on ampoule holder 130. In some embodiments, rotation of head holder 150 about guide pin 160 facilitates removal of material remaining in head 220 after ampoule 200 is broken. In some embodiments, head holder 150 is configured to rotate at least 90 degrees about guide pin 160 after head 220 is broken from body 210, for example, as depicted in FIG. 4B). In other embodiments, head holder 150 is configured to rotate less than 90 degrees about guide pin 160. In some embodiments, head holder 150 is configured to rotate greater than 90 degrees about guide pin 160, for example, between 90 and 180 degrees. In some embodiments, head holder 150 is configured to rotate at least or greater than 180 degrees. In some embodiments, head holder 150 rotates less than 180 degrees about guide pin 160. In some embodiments, head holder 150 includes an angled surface 158 configured to abut against an inner wall of housing 110 to limit rotation of head holder 150, as shown in FIG. 1C. In some embodiments, as shown in FIGS. 4A-4C, housing 110 includes an abutment surface 162 configured to abut against head holder 150 and angled to limit rotation of head holder 150 about guide pin 160. In some embodiments, abutment surface 162 is formed from wall 124 of housing 110 and is angled obliquely with respect to central longitudinal axis L1. In some embodiments, as shown in FIG. 4C, abutment surface 162 is configured to orient head holder 150 such that head 220 is angled towards outlet 116 of housing 110 when head holder 150 abuts against abutment surface 162.

Device 100 is preferably configured to minimize, prevent, or substantially prevent exposure of the user to the material released from ampoule 200 after ampoule 200 is opened, which may be particularly useful where the material may be toxic or noxious as in the case of certain volatile chemicals such as bone cement or adhesive components. Device 100 is also preferably configured to prevent exposure of the user to any sharp fragments (e.g., splinters or shards) created when head 220 is broken. In some embodiments, housing 110 of device 100 provides an enclosure configured to receive and contain the material released from ampoule 200 after ampoule 200 is opened. In some embodiments, housing 110 is further configured to minimize, prevent, or substantially prevent exposure of the user to the material received therein from ampoule 200. It is also preferred that housing 110 be configured to contain any fragments (e.g., splinters or shards) of ampoule 200 created when ampoule 200 is broken open. In some embodiments, housing 110 is configured to enclose any sharp edges of ampoule 200 (e.g., broken edges) formed when ampoule 200 is opened to prevent exposure of the user thereto. In some embodiments, housing 110 includes an inner wall that defines an interior space 112 that is configured to receive the material release from ampoule 200. In some embodiments, interior space 112 has a volume equal to or greater than the volume of ampoule 200. In some embodiments, housing 110 is made from a substantially rigid material. In some preferred embodiments, housing 110 is at least partially made from a transparent material to allow visual inspection of interior space 112 by the user. In some embodiments, housing 110 is constructed from a substantially rigid, clear plastic material. In other embodiments, housing 110 is made of glass.

As described herein, device 100 is preferably configured so that ampoule 200 is enclosed by housing 110 when ampoule 200 is opened so that housing 110 may contain any ampoule fragments (e.g., splinters or shards) and receive the material from ampoule 200. In some embodiments, head 220 is positioned in interior space 112 when head 220 is separated from body 210. In some embodiments, the material in body 210 and/or head 220 falls by gravity into interior space 112 after ampoule 200 is open. In some embodiments, the material removed from head 220 by rotating or pivoting head holder 150 as described herein is received in interior space 112. In some embodiments, material is withdrawn from body 210 and/or head 220 by creating a reduction in pressure within interior space 112, at least temporarily, after head 220 is broken from body 210. In some embodiments, the reduction in pressure within interior space 112 is created by exposing interior space 112 to a vacuum source. In other embodiments, returning ampoule holder 130 substantially to the initial position (e.g., by biasing element 140) creates a pressure decrease within interior space 112 sufficient to withdraw liquid material from body 210 and/or head 220.

Referring again to FIGS. 1A-4C, in some embodiments, housing 110 includes a base portion 120 for collecting the material released into interior space 112 from ampoule 200 (e.g., from separate head 220 and body 210). In some embodiments, base portion 120 is integrally formed with inlet portion 114. In other embodiments, base portion 120 and inlet portion 114 are formed separately and joined together. In some embodiments, housing 110 includes one or more seals 128 disposed between inlet portion 114 and base portion 120 to substantially prevent passage of material and/or fumes between inlet portion 114 and base portion 120. In some embodiments, base portion 120 includes walls 124 disposed about interior space 112. In some embodiments, at least a portion of walls 124 are transparent to allow visual inspection of interior space 112 by the user, for example, to visually determine the amount of material contained therein. In some embodiments, walls 124 includes portions that are substantially parallel to central longitudinal axis L1 and which may be configured to be symmetric, for example, as depicted in FIGS. 1A-2. In other embodiments, as shown in FIGS. 4A-4C, base portion 120 may have an asymmetric configuration.

According to certain embodiments, device 100 is configured to transfer material discharged from ampoule 200 to a second device, such as second device 300. Second device 300 may have any configuration suitable for receiving the material contained in ampoule 200. In some embodiments, device 100 includes a coupling for attachment to second device 300 to facilitate transfer of material thereto. In some embodiments, second device 300 is attached to device 100 prior to operating device 100 to open ampoule 200. In some embodiments, second device 300 is a mixing chamber or system. In some embodiments, second device is a vial, bottle, or other container. In some embodiments, second device 300 is a syringe barrel. In some embodiments, second device 300 contains a second material configured to be combined with the material contained in ampoule 200. For example, in one embodiment, the material in ampoule 200 is a first component of a two-component surgical bone cement system (e.g., a liquid monomer) and second device 300 contains the second bone cement component to be reacted therewith to form a surgical bone cement. In another example, the material in ampoule 200 and the second material contained in second device 300 are components of a multi-component adhesive system.

To facilitate transfer of material to second device 300, in some embodiments of device 100 base portion 120 includes an outlet 116 in fluid communication with interior space 112. Outlet 116 is preferably configured to provide an exit for the material received from ampoule 200. In some embodiments, outlet 116 is the only exit through which material from ampoule 200 may egress from device 100. According to some embodiments outlet 116 is configured for attachment to second device 300 to allow transfer of material thereto. For example, in some embodiments, outlet 116 includes a coupling, such as a Luer taper or other fitting, for coupling with second device 300. Preferably, outlet 116 includes a coupling configured to form a liquid and/or vapor-tight seal with second device 300. In some embodiments, outlet 116 is positioned proximate a second end of housing 110. In some embodiments, outlet 116 is positioned on housing 110 opposite inlet portion 114. In some embodiments, outlet 116 is radially disposed about central longitudinal axis L1. In some embodiments, base portion 120 further includes a bottom interior surface 122 that may be configured to direct, channel, or funnel material toward outlet 116. For example, bottom interior surface 122 may be angled obliquely relative to central longitudinal axis L1 to direct material toward outlet 116. In some embodiments, device 100 further includes a filter 118 disposed between interior space 112 and outlet 116. In some embodiments, filter 118 is selected to have a pore size to allow passage of the material from interior space 112 to outlet 116 while preventing passage of shards or splinters from the broken ampoule 200 from interior space 112 to outlet 116.

The transfer of material from device 100 to second device 300 according to some embodiments may be facilitated by increasing the pressure within interior space 112, at least temporarily, relative to the pressure within second device 300. In some embodiments, a pumping action to facilitate transfer of material from device 100 to second device 300 can be achieved by rapidly pressing and releasing ampoule holder 130 several times such that ampoule holder 130 toggles between its first position and second position. In some embodiments, second device 300 can be disconnected from outlet 116 once transfer of the material from device 100 has been completed. Transfer of the material can be confirmed by visual inspection by the user, for example, if housing 110 is constructed from a transparent material. In some embodiments, device 100 is intended to be a single-use device and can be subsequently disposed of in accordance with procedures known in the art. In some embodiments, broken ampoule 200 remains safely contained within device 100 and can be disposed of therewith.

It should be understood that various changes, substitutions, and alterations can be made herein without departing from the spirit and scope of the invention as defined by the appended claims. It should also be apparent that individual elements identified herein as belonging to a particular embodiment may be included in other embodiments of the invention. Moreover, the scope of the present application is not intended to be limited to the particular embodiments of the process, machine, manufacture, and composition of matter, means, methods and steps described in the specification. As one of ordinary skill in the art will readily appreciate from the disclosure herein, processes, machines, manufacture, composition of matter, means, methods, or steps, presently existing or later to be developed that perform substantially the same function or achieve substantially the same result as the corresponding embodiments described herein may be utilized according to the present invention.

The invention claimed is:

1. A device for opening an ampoule containing a volume of a liquid, the ampoule including a body and a head, the device comprising:
   an ampoule holder configured and dimensioned to hold the body of the ampoule along a central longitudinal axis;
   a head holder configured and dimensioned to hold the head of the ampoule; and
   a guide engaged with the head holder and configured to direct the head holder to translate along the guide from an initial position on the central longitudinal axis to a secondary position offset from the central longitudinal axis when the ampoule holder is advanced in a first direction along the central longitudinal axis from a first position.

2. The device of claim 1, further comprising a housing defining an interior space for containing the head holder and the guide, the housing including a first end in sliding engagement with the ampoule holder and a second end proximate an outlet in fluid communication with the interior space.

3. The device of claim 2, further comprising a biasing element disposed between the ampoule holder and the housing, the biasing element configured to apply a force to the ampoule holder in a second direction opposite the first direction.

4. The device of claim 3, wherein the biasing element is configured to return the ampoule holder substantially to the first position.

5. The device of claim 1, wherein the guide defines a path for the head holder from the initial position to the secondary position, at least a portion of the path extending laterally and/or obliquely from the central longitudinal axis.

6. The device of claim 1, wherein the device is configured to break the head of the ampoule from the body of the ampoule when the head holder is directed from the initial position to the secondary position by the guide.

7. The device of claim 1, wherein the head holder includes a pivot, and wherein the head holder is configured to rotate about the pivot when the head holder is directed from the initial position to the secondary position by the guide.

8. The device of claim 1, wherein the guide includes a groove and wherein head holder includes a guide pin retained within the groove, the groove defining a path for the guide pin from the initial position to the secondary position.

9. The device of claim 8, wherein at least a portion of the groove extends laterally and/or obliquely relative to the central longitudinal axis.

10. The device of claim 8, wherein the head holder rotates about the guide pin when the head holder is directed from the initial position to the secondary position by the guide.

11. The device of claim 1, wherein the guide includes a rigid plane disposed at an oblique angle relative to the central longitudinal axis.

12. The device of claim 11, wherein the head holder is configured to abut against and translate along the rigid plane when the ampoule holder is advanced in the first direction along the central longitudinal axis from the first position.

13. The device of claim 1, wherein the head holder is configured to invert the head of the ampoule when the head holder is directed from the initial position to the secondary position and the head holder is configured to retain the head when the head is inverted.

14. The device of claim 1, wherein the guide is separate from the head holder.

15. The device of claim 14, wherein the guide is separate from the housing.

16. The device of claim 14, wherein the guide is configured such that, when the head holder translates along the guide, an entirety of the head holder translates away from ampoule holder.

17. The device of claim 14, wherein the device includes a housing having a wall disposed about an interior space, and the guide and head holder are disposed within the interior space.

18. The device of claim 2, further comprising a seal disposed between the ampoule holder and the housing, the seal configured to substantially prevent passage of vapor or liquid between the ampoule holder and the housing.

19. The device of claim 2, further comprising a filter disposed between the interior space and the outlet, the filter having a pore size sufficient to allow passage of the liquid from the interior space to the outlet and to prevent passage of ampoule fragments from the interior space to the outlet.

20. The device of claim 2, wherein the device is configured such that advancement of the ampoule holder in the first direction along the central longitudinal axis creates a pressure increase within the interior space.

21. The device of claim 4, wherein returning the ampoule holder substantially to the initial position creates a pressure decrease within the interior space.

22. The device of claim 21, wherein the pressure decrease is sufficient to draw liquid from the ampoule to the interior space.

23. A manually-operated device for breaking an ampoule comprising:
- an ampoule containing a liquid, the ampoule including a body and a head disposed about a central longitudinal axis;
- a housing having a wall disposed about an interior space;
- an ampoule holder in sliding engagement with the housing and secured to the body of the ampoule, the ampoule holder movable relative to the housing;
- a head holder pivotably secured to the housing and secured to the head of the ampoule within the interior space, the head holder configured to transition from an initial position on the central longitudinal axis to a secondary position offset from the central longitudinal axis to break the head of the ampoule from the body of the ampoule; and
- a guide engaged with the head holder and configured to direct the head holder to translate along the guide from the initial position to the secondary position when the ampoule holder is advanced along the central longitudinal axis from a first position by manual pressure.

24. The device of claim 23, further comprising a biasing element disposed between the ampoule holder and the housing, the biasing element configured to bias the ampoule holder toward the first position when the manual pressure is released.

25. The device of claim 23, wherein the guide includes a groove and wherein the head holder includes a guide pin retained within the groove, the groove defining a path for the guide pin from the initial position to the secondary position.

26. The device of claim 25, wherein at least a portion of the groove extends laterally and/or obliquely relative to the central longitudinal axis.

27. The device of claim 25, wherein the head holder is configured to rotate at least 90 degrees about the guide pin when the head holder is directed from the initial position to the secondary position by the guide.

28. The device of claim 23, wherein the guide includes a rigid plane disposed at an oblique angle relative to the central longitudinal axis.

29. The device of claim 28, wherein the head holder is configured to abut against and translate along the rigid plane when the ampoule holder is advanced in the first direction along the central longitudinal axis from the first position.

30. The device of claim 23, wherein the head holder includes a pivot, and the head holder is configured to rotate about the pivot when the head holder is directed from the initial position to the secondary position by the guide.

31. The device of claim 23, wherein the head holder is configured to invert the head of the ampoule when the head holder is directed from the initial position to the secondary position and the head holder is configured to retain the head when the head is inverted.

32. The device of claim 23, wherein the guide is separate from the head holder.

33. The device of claim 32, wherein the guide is separate from the housing.

34. The device of claim 32, wherein the guide is configured such that, when the head holder translates along the guide, an entirety of the head holder translates away from ampoule holder.

35. The device of claim 32, wherein the guide is disposed within the interior space.

* * * * *